(12) United States Patent
Brooks

(10) Patent No.: US 9,204,951 B2
(45) Date of Patent: Dec. 8, 2015

(54) PROTECTIVE CONTAINER FOR ORAL APPLIANCES

(71) Applicant: Patricia M Brooks, Escondido, CA (US)

(72) Inventor: Patricia M Brooks, Escondido, CA (US)

(*) Notice: Subject to any disclaimer, the term of this patent is extended or adjusted under 35 U.S.C. 154(b) by 219 days.

(21) Appl. No.: 13/804,778

(22) Filed: Mar. 14, 2013

(65) Prior Publication Data

US 2014/0263500 A1    Sep. 18, 2014

Related U.S. Application Data

(60) Provisional application No. 61/619,419, filed on Apr. 3, 2012.

(51) Int. Cl.
| | |
|---|---|
| *A45C 11/00* | (2006.01) |
| *A61C 19/02* | (2006.01) |
| *A46B 15/00* | (2006.01) |
| *A61C 7/00* | (2006.01) |

(52) U.S. Cl.
CPC .............. *A61C 19/02* (2013.01); *A46B 15/0091* (2013.01); *A61C 7/00* (2013.01)

(58) Field of Classification Search
USPC ......... 206/63.5, 424; 224/660, 651, 652, 245, 224/246, 677, 269
See application file for complete search history.

(56) References Cited

U.S. PATENT DOCUMENTS

| | | | | |
|---|---|---|---|---|
| 1,533,694 | A | * | 4/1925 | Chapman ..................... 206/449 |
| 2,163,862 | A | | 6/1939 | Wing |
| 2,620,919 | A | | 8/1950 | Passmore |
| 4,666,037 | A | | 5/1987 | Weissman |
| 4,697,700 | A | | 10/1987 | Weissman |
| 4,934,534 | A | * | 6/1990 | Wagner ......................... 206/568 |
| 4,966,319 | A | * | 10/1990 | Fleming ........................ 224/615 |
| D425,295 | S | * | 5/2000 | Borja et al. ................. D3/203.1 |
| 6,247,730 | B1 | * | 6/2001 | Henderson et al. ............. 281/51 |
| 6,305,591 | B1 | | 10/2001 | Jones |
| 6,467,619 | B1 | * | 10/2002 | Leen et al. .................... 206/421 |
| 7,201,271 | B1 | * | 4/2007 | Saad ............................ 206/63.5 |
| D553,795 | S | | 10/2007 | Tran |
| D563,561 | S | | 3/2008 | Faust |
| 2002/0166881 | A1 | * | 11/2002 | Willingham et al. ......... 224/652 |
| 2004/0144819 | A1 | * | 7/2004 | Huang ........................... 224/583 |
| 2006/0076250 | A1 | * | 4/2006 | Kwasney ........................ 206/83 |

OTHER PUBLICATIONS

Ortho Technology, Inc. Ortho Technology 2013 Product Catalog p. 158 www.orthotechnology.com Ortho Technology, Inc. 17401 Commerce Park Blvd, Tampa, FL 33647, Date 2013.

* cited by examiner

*Primary Examiner* — Brian D Nash
*Assistant Examiner* — Corey Skurdal
(74) *Attorney, Agent, or Firm* — Gerard Carlson, Agent

(57) ABSTRACT

A closeable clam shell type container with a retaining cord provides a protective enclosure for the storage and transport of oral appliances. A strap and clip allow the container to be attached to clothing and packs. Material choices allow versions that are machine washable. Some versions include a removable hard inner liner to provide further protection of oral appliances.

16 Claims, 13 Drawing Sheets

PROTECTIVE CONTAINER FOR ORAL APPLIANCES

CROSS REFERENCE TO RELATED APPLICATIONS

This application claims the benefit of the provisional application entitled "Protective Container for Oral Appliances"by Patricia M. Brooks, Ser. No. 61/619,419 filed on Apr. 3, 2012 and is hereby incorporated by reference in its entirety.

FEDERALLY SPONSORED RESEARCH OR DEVELOPMENT

Not applicable.

JOINT RESEARCH AGREEMENT

Not applicable

SEQUENCE LISTING

Not applicable

FIELD OF THE INVENTION

The present invention relates to the field of containers for oral appliances.

BACKGROUND OF THE INVENTION

Currently a of number oral appliances exist for use in orthodontia, prosthetics and protection. There is a need for securing and protecting these appliances when not in use. There is also a need for enabling easy user access to these appliances when needed.

SUMMARY OF THE INVENTION

In one embodiment, the protective container for oral appliances, also referred to simply as the container, has an outer zip-able cover. The outer zip-able cover is like a clam shell with two halves hinged in the back closing with a zipper at the sides and front. A strap attached to the container at the back near the hinge provides a way to attach the container via a clip to a belt, belt loop, back pack or the like. This allows the container to be easily carried reducing the risk of loss. When the container is unzipped and opened, a retaining cord is exposed. This retaining cord is attached to the interior at the back of the container approximately parallel to the inside surface of the hinge.
The retaining cord is useful for constraining an oral appliance from falling out of an open container. Examples of oral appliances include, but are-not limited to, mouth guards, retainers, dental braces, dentures, bridges and prosthetics.

In another embodiment, a hard inner liner, also clam shell in shape, fits inside the container. The oral appliance fits inside this hard inner liner. The hard inner liner adds additional protection to the oral appliance reducing possibility of crushing or breakage if the container is dropped or stepped upon. The hard inner liner is also hinged at the rear. The hard inner liner further has a notch at opposite sides of the liner hinge to allow the retaining cord to fit inside the liner. This allows the hard inner liner to close more tightly. The retaining cord acts to constrain both the hard inner liner and the oral appliance inside the container. The combination of the pieces allows for easy storage and retrieval. The retaining cord on the inside of the container holds the hard inner liner securely in the zip-able cover.

In another embodiment, the container has a mesh net pouch attached to one or both sections of the clam shell to provide storage for dental supplies. Examples of dental supplies include, but are-not limited to, floss, toothpicks, dental wax or gum. An elastic cord at the open end of the mesh net pouch acts to retain the dental supplies in the pouch.

BRIEF DESCRIPTION OF THE DRAWINGS

The summary above, and the following detailed description will be better understood in view of the enclosed figures which depict details of various embodiments. It should however be noted that the invention is not limited to the precise arrangement shown in the drawings and that the drawings are provided merely as examples. Like reference numerals refer to like parts.

DETAILED DESCRIPTION

Figure 1:
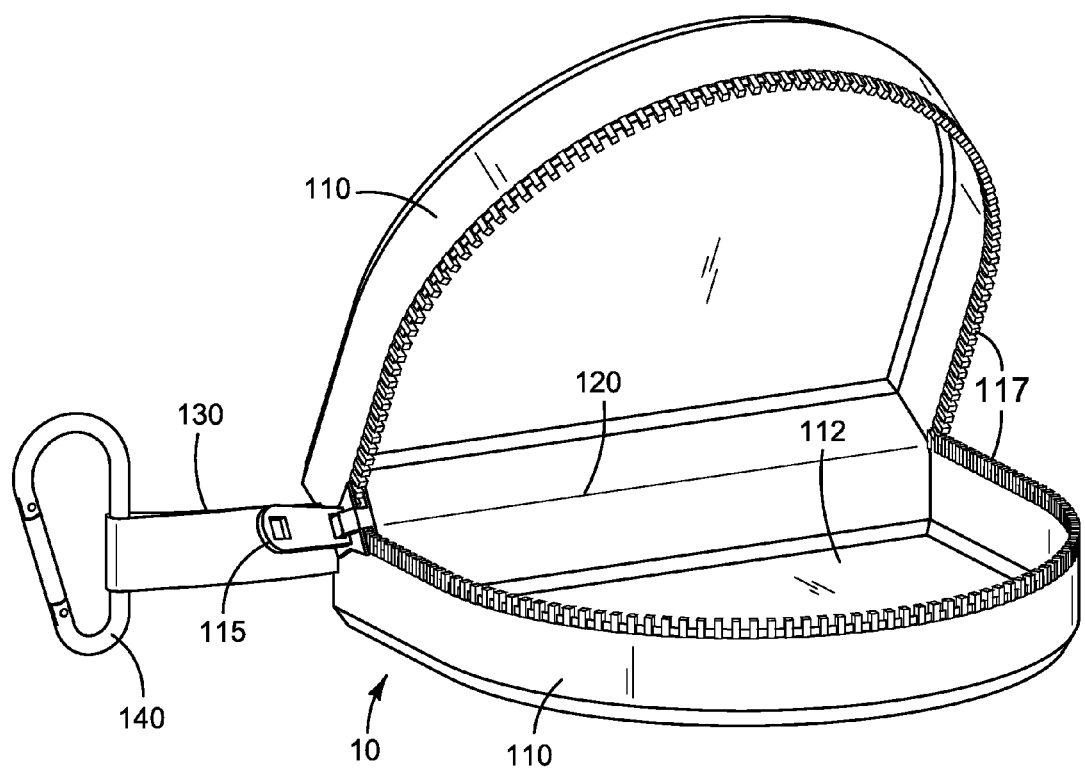
FIG. 1 shows one embodiment of the container in the open position.

FIG. 1 shows one embodiment of the protective container for oral appliances 10 with the outer zip-able cover arranged as two clam shell halves also called container halves 110. A zipper handle 115 zips together the zipper teeth 117 to close the outer zip-able cover halves 110. The outer zip-able cover halves meet in the back at a hinge 120 which enables the container halves 110 to open allowing access to the interior space of the container 112. In one embodiment, the two clam shell halves and the hinge are formed from a single piece of material. In other embodiments the two container halves and hinge can be separate pieces that are joined together. The term clam shell or clam shell like is not be understood as specifying a particular shape, as many shapes are possible. While a zipper is shown in the following figures, other types of closures such as hook and latch, button and hole, and other types of closures are also possible A strap 130 is secured to the cover at the back near the hinge 120. A clip 140 attached to the strap 130 allows the container 10 to be attached to a belt, belt loop, backpack, luggage or other items. This attachment reduces the risk of loss.

In use, the user unzips the zipper 115 and opens the two cover halves 110 providing access to the interior 112 of the container 10. The user then places the oral appliance and possible accessories or dental supplies into the interior 112 of the container 10 and closes the zipper 115. The user then attaches or clips the container 10 to an article of clothing, a backpack, fanny pack or other item for safe-keeping and transport. The strap 130 and clip 140 enable the container 10 to be securely transported while reducing the risk of loss.

Figure 2:
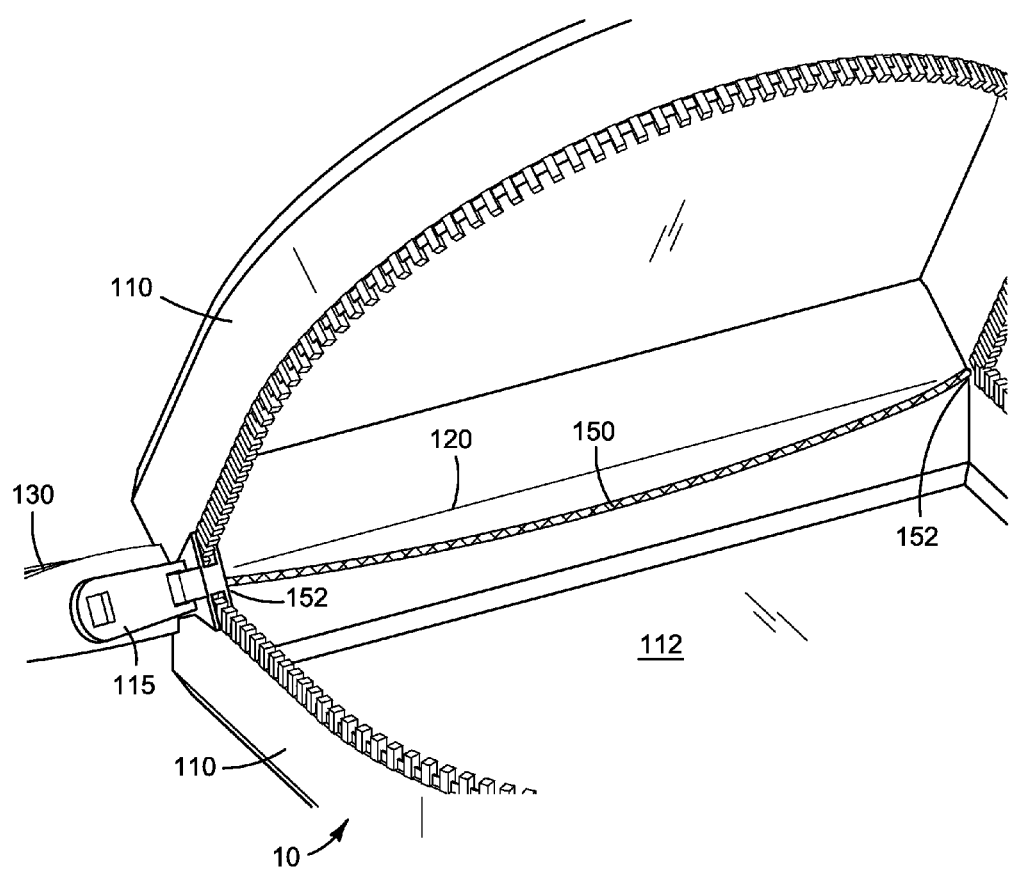
FIG. 2 shows a close-up of one embodiment of the container emphasizing the retaining cord.

FIG. 2 shows a close-up of one embodiment of the container 10 with a retaining cord 150. The retaining cord is typically made of a stretchable elastic material, making it an elastic retaining cord, but it can be made of other materials. The retaining cord 150 is anchored at both corners 152 of the cover halves 110 near the hinge 120. The elastic retaining cord 150 is stretched or tensioned across the hinge 120 in the interior space 112. The retaining cord 150 can be pulled out from proximity with the hinge 120 while an oral appliance is placed in the interior space 112 of the container 10. The elasticity of the retaining cord 150 restrains the oral appliance (not shown) toward the hinge 120 and reduces the risk of the oral appliance falling out of the container 10.

In use, the user simply pulls the retaining cord 150 away from the hinge 120 and loops the retaining cord 150 over or around the oral appliance. Once released, the natural elasticity of the retaining cord 150 holds the oral appliance against the hinge 120 and the interior 112 of the container 10.

Figure 3:
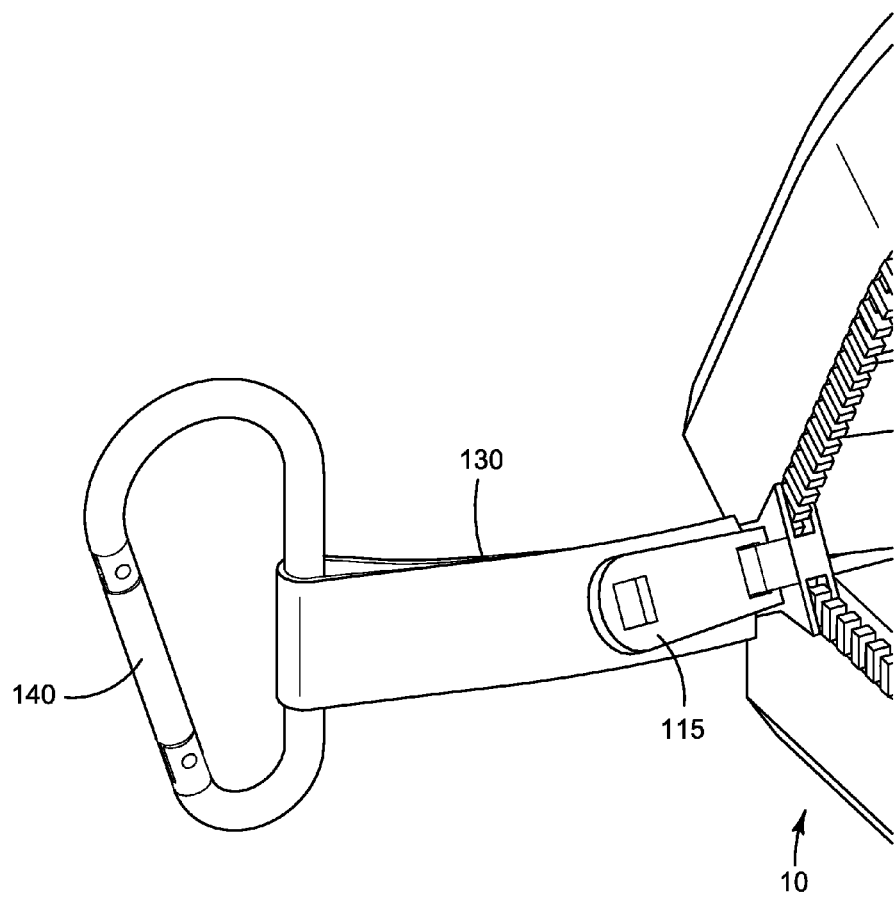
FIG. 3 shows a close-up of one embodiment of the container emphasizing the strap and clip.

FIG. 3 shows a detail of the strap 130 and clip 140 of one embodiment of the container 10. The strap 130 attaches to the container 10 and the outer zip-able cover halves 110 near the hinge 120 of FIGS. 1 and 2. The strap can be made of a number of materials including but not limited to, an elastic loop, a braid, a cord or an extension of the hinge material itself. The clip 140 is depicted as a carabiner. Other versions of clip 140 are possible.

Figure 4:
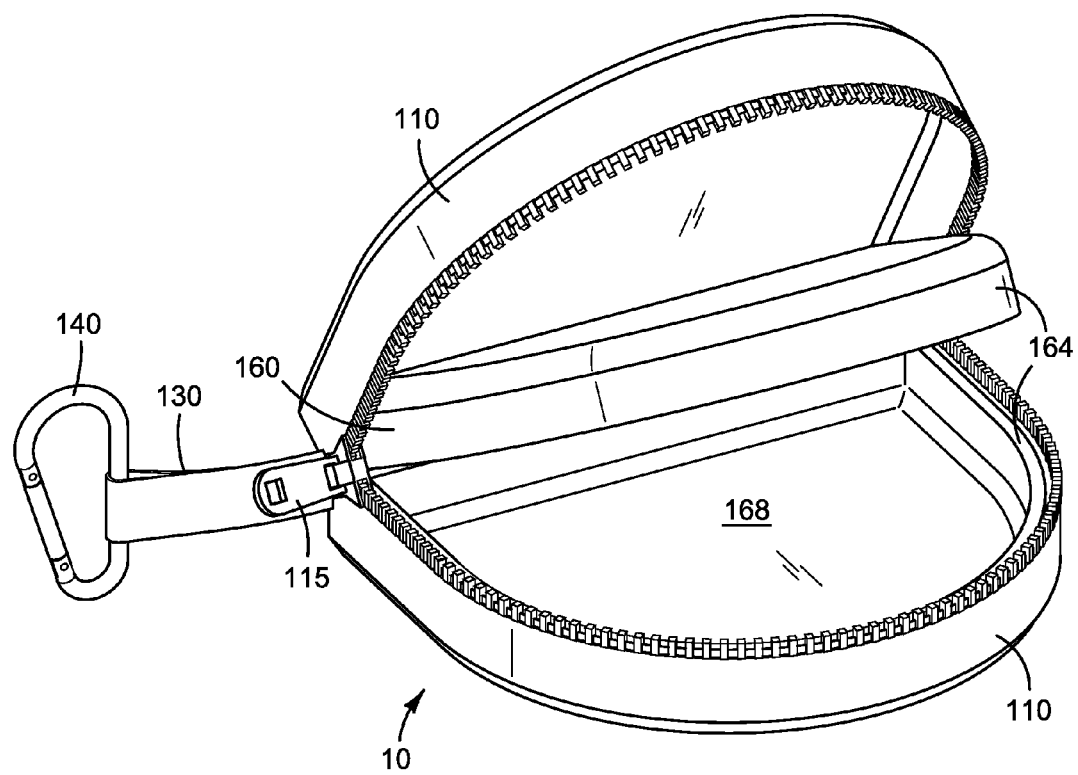
FIG. 4 shows an embodiment of the container with the removable hard inner liner fitted in the container.

FIG. 4 shows one embodiment of the container 10 with a removable hard inner liner 160. The container 10 may be used with or without the hard removable inner liner 160. The hard removable inner liner 160, or simply liner 160 for short, is similar to the outer zip-able cover halves 110 in that it also has two clam shell like halves 164 that come together to enclose the liner interior 168. The liner 160 can be made of a single piece of plastic with a live hinge and compliant catch to hold it closed. Other versions of the liner 160 can be made of metal with other types of hinges and closures. Other embodiments of the liner 160 can use the outer zip-able cover halves 110 of FIG. 1 to hold the liner closed when the zip-able halves force the liner halves 164 together.

Figure 5:
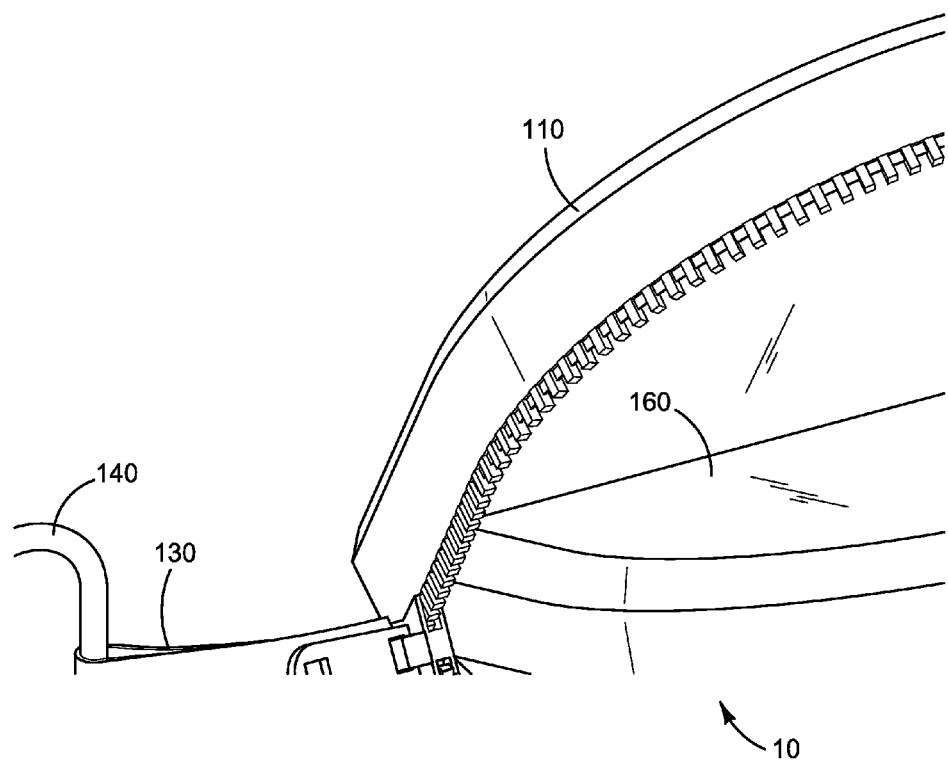
FIG. 5 shows a close-up of one embodiment of the container emphasizing a portion of the removable hard inner liner.

FIG. 5 shows a close up view of one embodiment of the removable hard inner liner 160 fitted into the outer zip-able cover halves 110 of the container 10.

Figure 6:
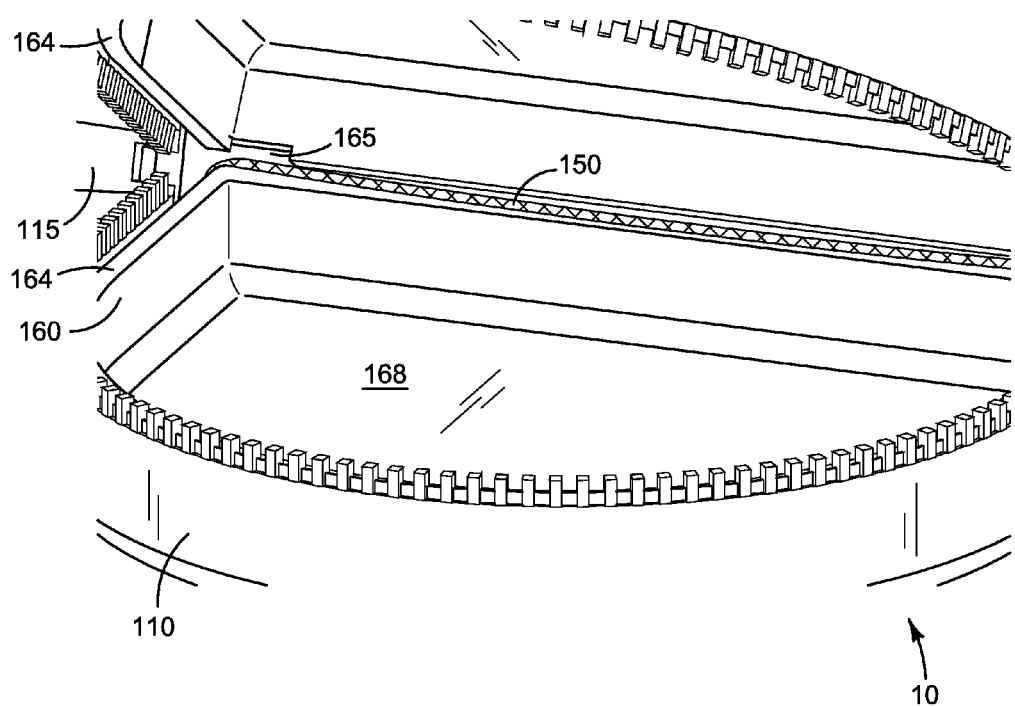
FIG. 6 shows a close-up of one embodiment of the container emphasizing a portion of the removable hard inner liner.

FIG. 6 shows a close up view of one embodiment of the removable hard inner liner 160 fitted into the outer zip-able cover halves 110 of the container 10 of FIGS. 1 and 2. The hard inner liner, simply called the liner, 160 is composed of two removable hard inner liner halves 164. Notches 165, of which one is shown, are near the hinge area in the liner interior 168. The retaining cord 150 passes through the notch 165 into the interior of the liner 168 to retain the liner inside the container 10. The retaining cord 150 can be used simultaneously to hold an oral appliance, not shown, inside the liner.

Figure 7:
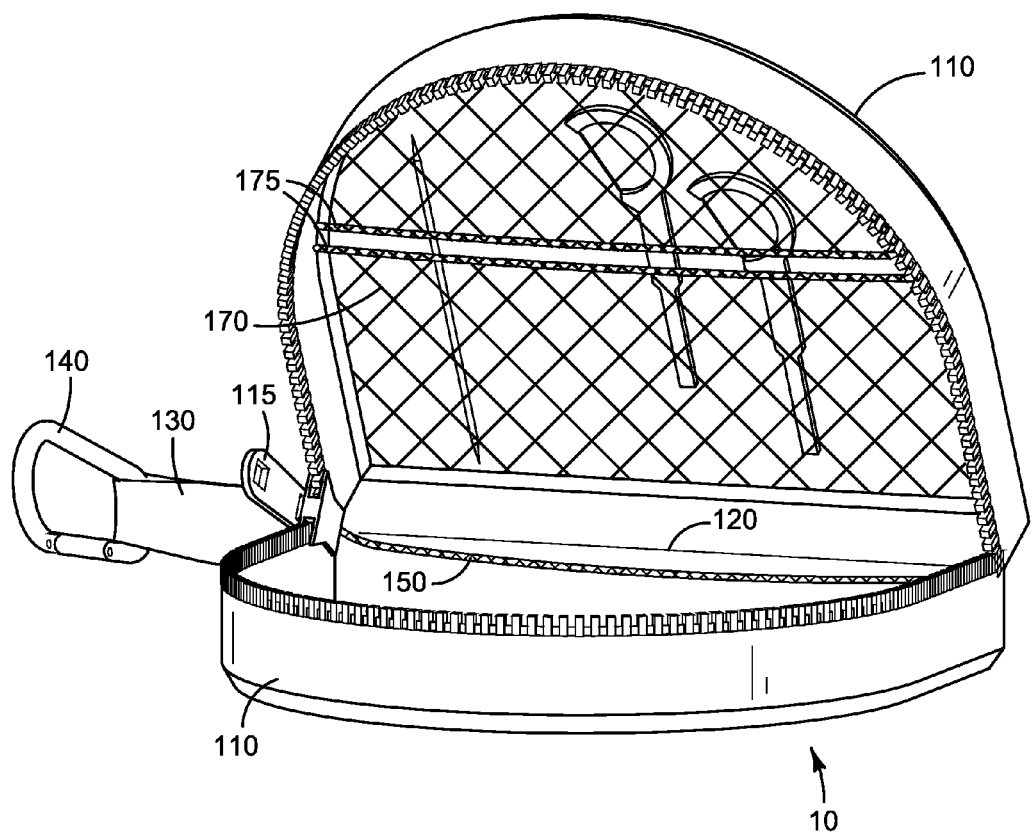
FIG. 7 shows another embodiment of the container with a net mesh pouch and elastic lip.

FIG. 7 shows a view of one embodiment of the container 10 with a mesh net pouch 170 on one of the outer zip-able cover halves 110. The mesh net pouch 170 has one or more elastic lips 175 to help keep the contents of the mesh net pouch 170 from falling out. In another embodiment the container has a mesh net pouch attached to one or both sections of the clam shell to provide storage for dental supplies or accessories. While a mesh net pouch is shown in FIG. 7, other types of pouches are possible. For example a solid fabric pouch or pleated pouch with an elastic lip for closure can be used in conjunction with or in place of the mesh net pouch. Examples of dental supplies include, but are not limited to, floss, toothpicks, dental wax or gum. In FIG. 7 the contents are depicted as a toothpick and two floss devices.

In use, the user opens the container 10 to expose the mesh net pouch 170. The user pulls the elastic lip or lips 175 away from the mesh net pouch 170 to place materials into, or retrieve materials from, the mesh net pouch 170.

Figure 8:
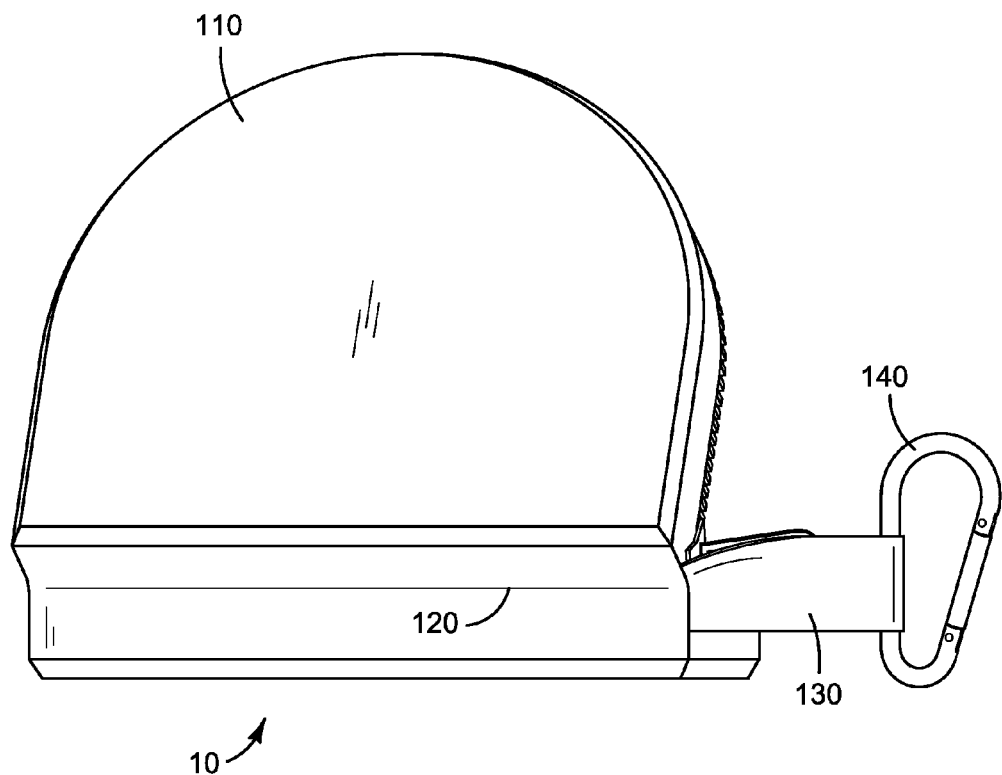
FIG. 8 shows an embodiment of the rear of the container and the hinge.

FIG. 8 shows a rear view of one embodiment of the container 10.

Figure 9:
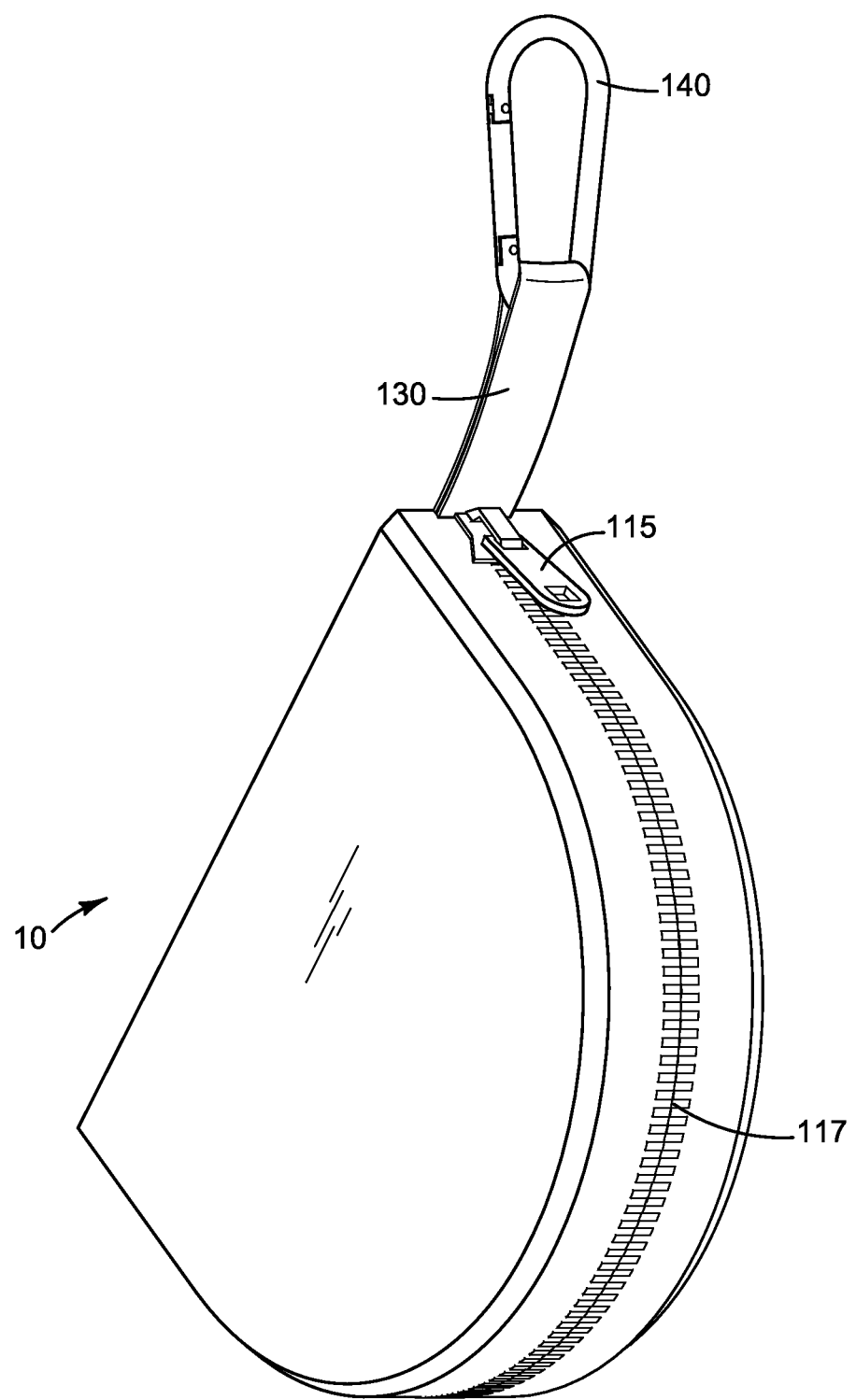
FIG. 9 shows an embodiment with the closed zipper adjacent the strap.

FIG. 9 shows an embodiment where the zipper handle 115, in the closed position is adjacent the strap 130 and clip 140. In this embodiment, when the container 10 is worn on the waist for example, a user can unzip the zipper handle 115 without removing, unclipping or repositioning the container 10.

Figure 10:
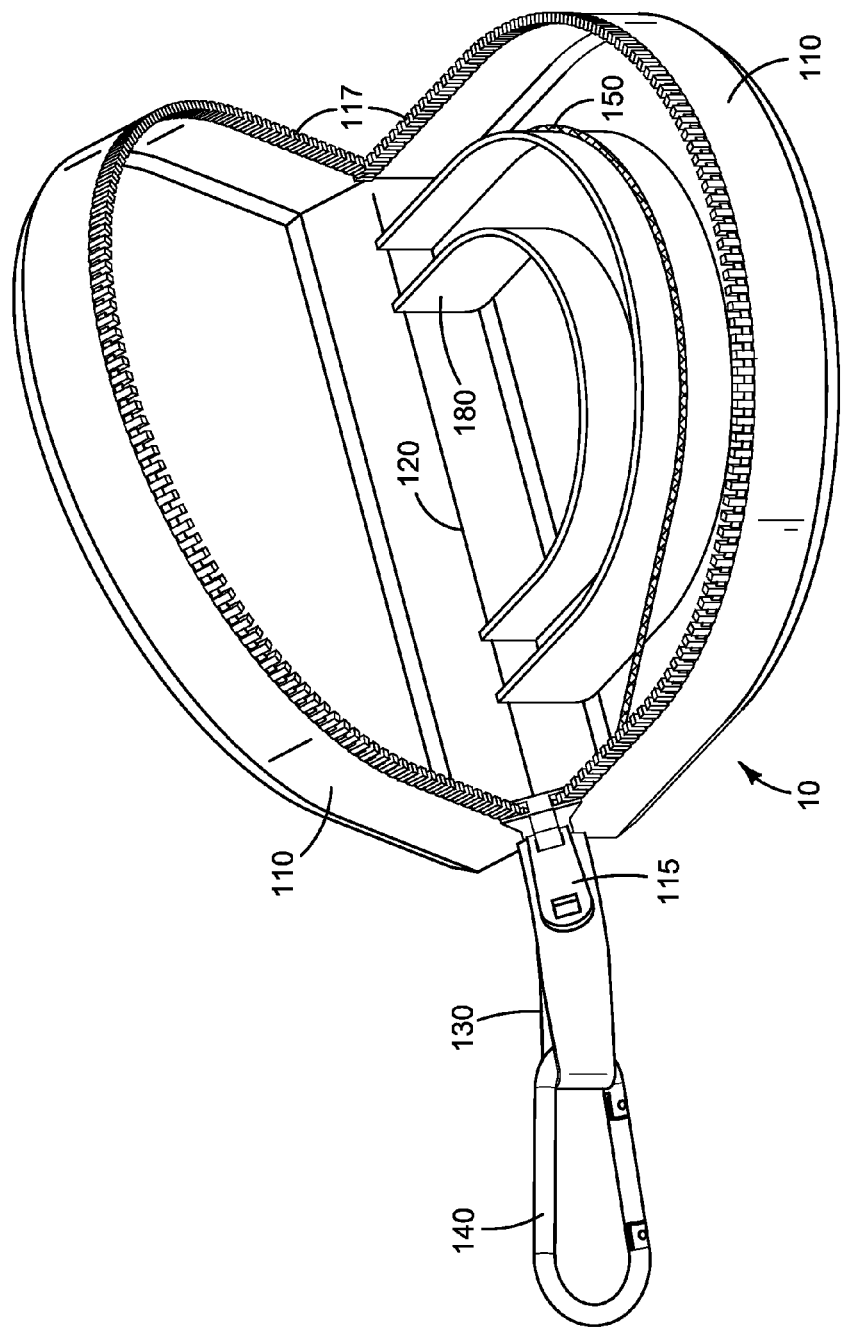
FIG. 10 shows an embodiment with an oral appliance.

FIG. 10 shows an oral appliance 180 inside the container 10. The elastic retaining cord 150 stretches across the oral appliance 180 and holds it inside the container 10. In this configuration, the container 10 can be opened in any position without the oral appliance falling out. In some embodiments, the oral appliance 180 can even be retrieved with one hand. Note that in FIG. 10 the oral appliance is depicted as a mouth guard. Examples of other oral appliances include, but are not limited to, retainers, dentures, partials, bridges, orthodontic head gear.

Figure 11:
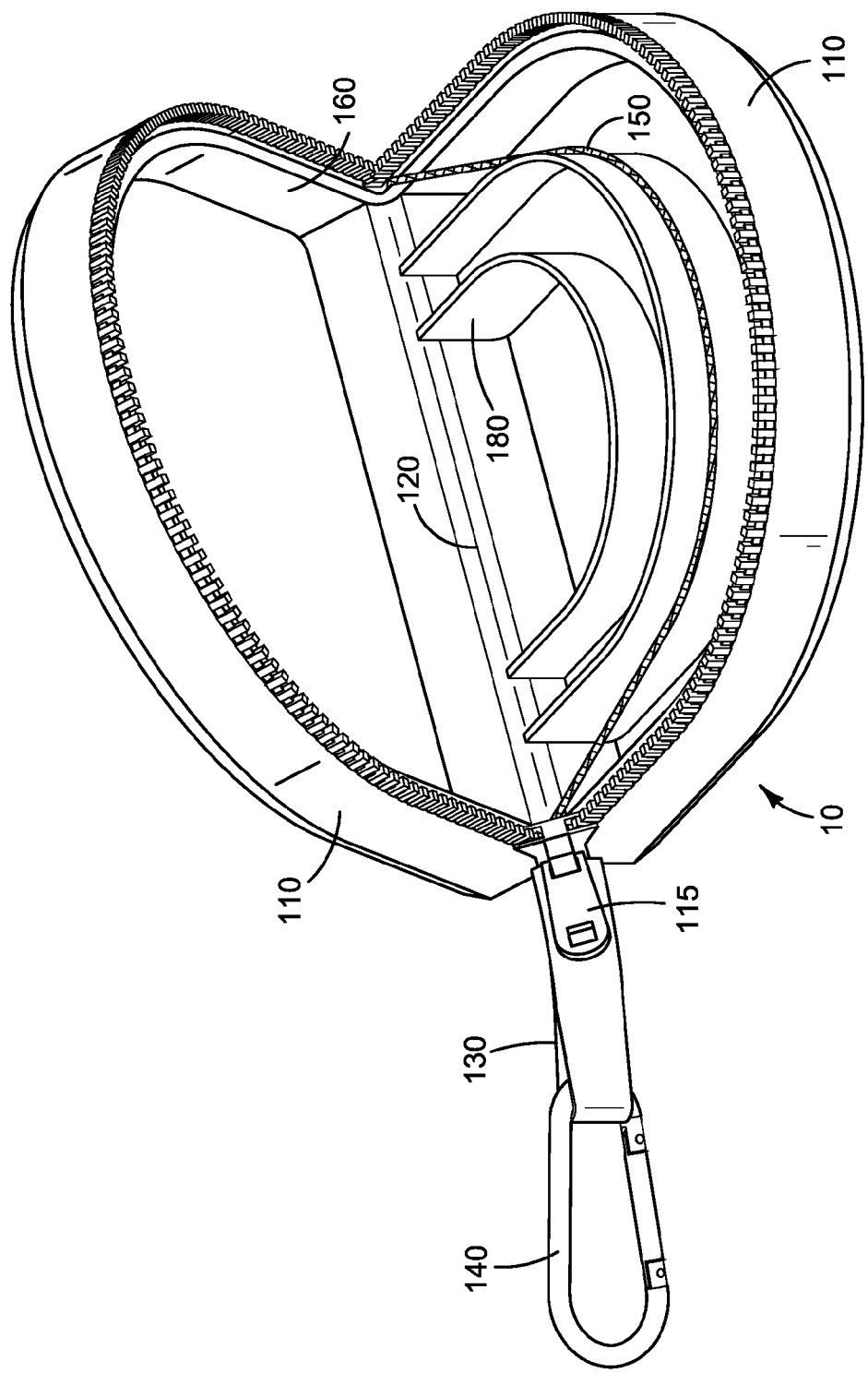
FIG. 11 shows an embodiment with an oral appliance inside a liner.

FIG. 11 shows an oral appliance 180 inside a liner 160 which is itself inside the container 10. The elastic retaining cord 150 stretches across the oral appliance 180 and holds it inside the liner 160. This resulting tension also holds the liner 160 inside the container 10. In this configuration, the container 10 can still be opened in any position without the oral appliance falling out. The liner 160 also is restrained inside the container 10. There are environments where a user may choose to have additional protection of the oral appliance. In such cases, the liner 160 can be employed. In situations where the extra protection is not required, the container 10 can be used without the liner 160. In some embodiments, the oral appliance 180 can even be retrieved with one hand, while the liner 160 remains constrained in the container 10.

Figure 12:
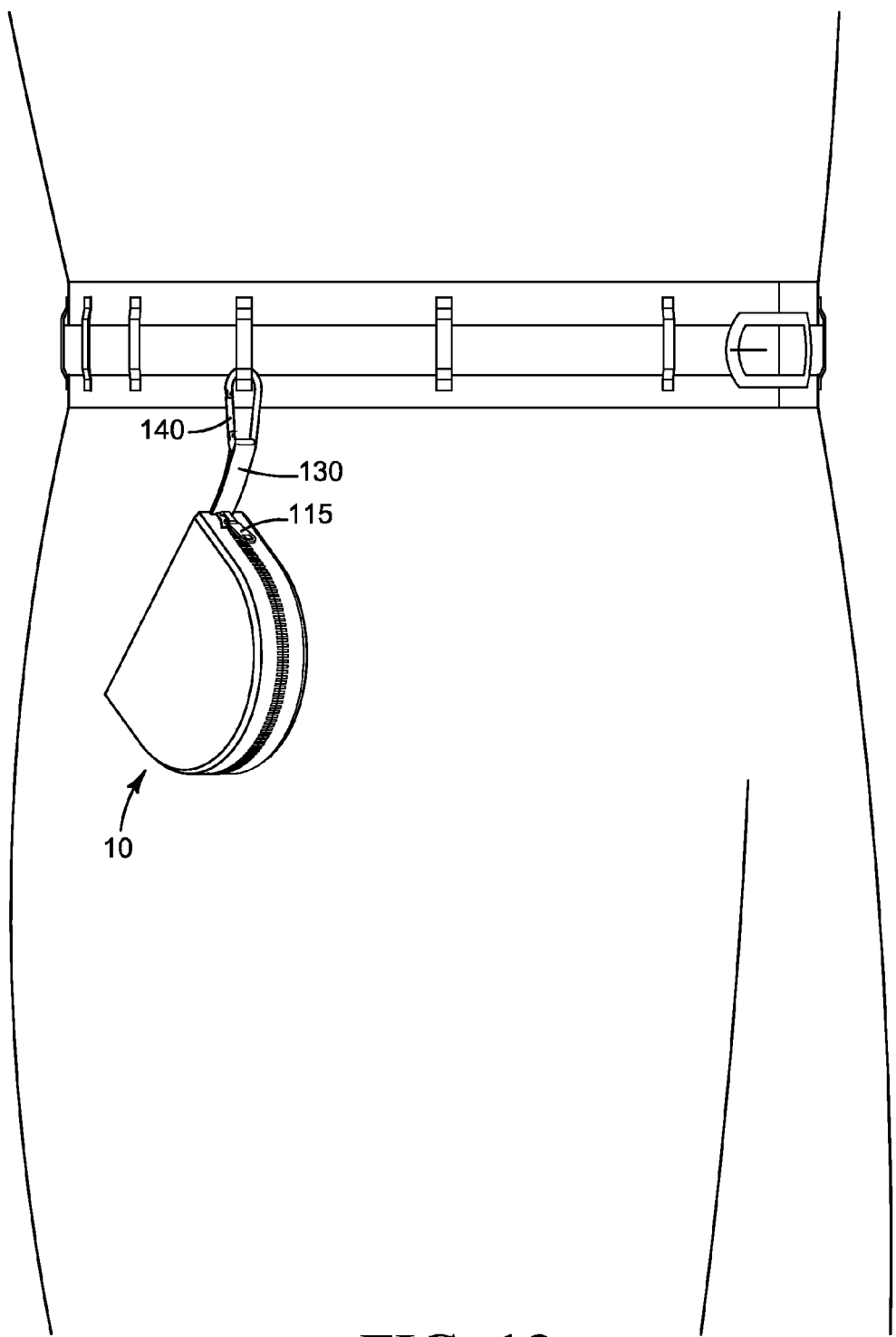
FIG. 12 shows one use of an embodiment worn on the waste of a user.

FIG. 12 shows one situation described for FIGS. 10 and 11. In FIG. 12, the container 10 is suspended from a belt or belt loop of a user. The clip 140 attaches to the belt or belt loop and the container 10 hangs from strap 130. In this situation, the zipper handle 115 is in the closed position when the zipper handle is adjacent the strap 130. A simple downward pull on the zipper handle 115 allows the user to open the container 10, in many cases, with just one hand.

Not only are metals such as aluminum, steel, brass and other alloys suitable, but also many different types of plastics, polymers, fabrics and composites work well. A mix of materials is also possible. For example the outer zip-able cover halves 110 can be of a fabric, plastic or a combination of the two. The removable hard inner liner 160 can be made of plastics, metals or other materials. Materials can be man-made or natural.

Material sets can be chosen for all components; container 10, outer zip-able halves 110, zipper 115, and teeth 117, hinge 120, strap 130, clip 140, retaining cord 150, removable hard inner liner 160, mesh net pouch 170 and elastic lip 175 so that the container 10 and all components are washable. For example a material set can be chosen so that the container 10 and components can be put into a washing machine. Furthermore, the hinge 120 can be made from a number of materials. The hinge could be the same material as the outer zip-able halves 110, a separate hinge assembly, a stretchable or expandable material, or a number of other implementations known to those skilled in the art.

There are a number of ways of protecting and containing oral appliances 180 with the embodiments described above. In one method, the user places the oral appliance 180 into the interior space 112 of the closable clam-shell like container 10, and retains the oral appliance 180 inside the interior space 112 with the elastic retaining cord 150. The user then closes the container 10, and attaches the container to clothing or luggage with the strap 130 and clip 140.

In another method the user places the oral appliance 180 in a remove-able hard inner liner 160, and fits the liner 160 into the interior space 112 of the container 10 constraining both the oral appliance 180 and remove-able hard inner liner 160 inside the interior space 112 with the elastic retaining cord 150.

In still another method of use, the user stores dental supplies or accessories of the oral appliance 180 in a pouch 170 attached inside the interior space 112. The pouch 170 contains items inside the container interior 112, while the elastic lip 175 keeps the items within the pouch 170.

Figure 13:
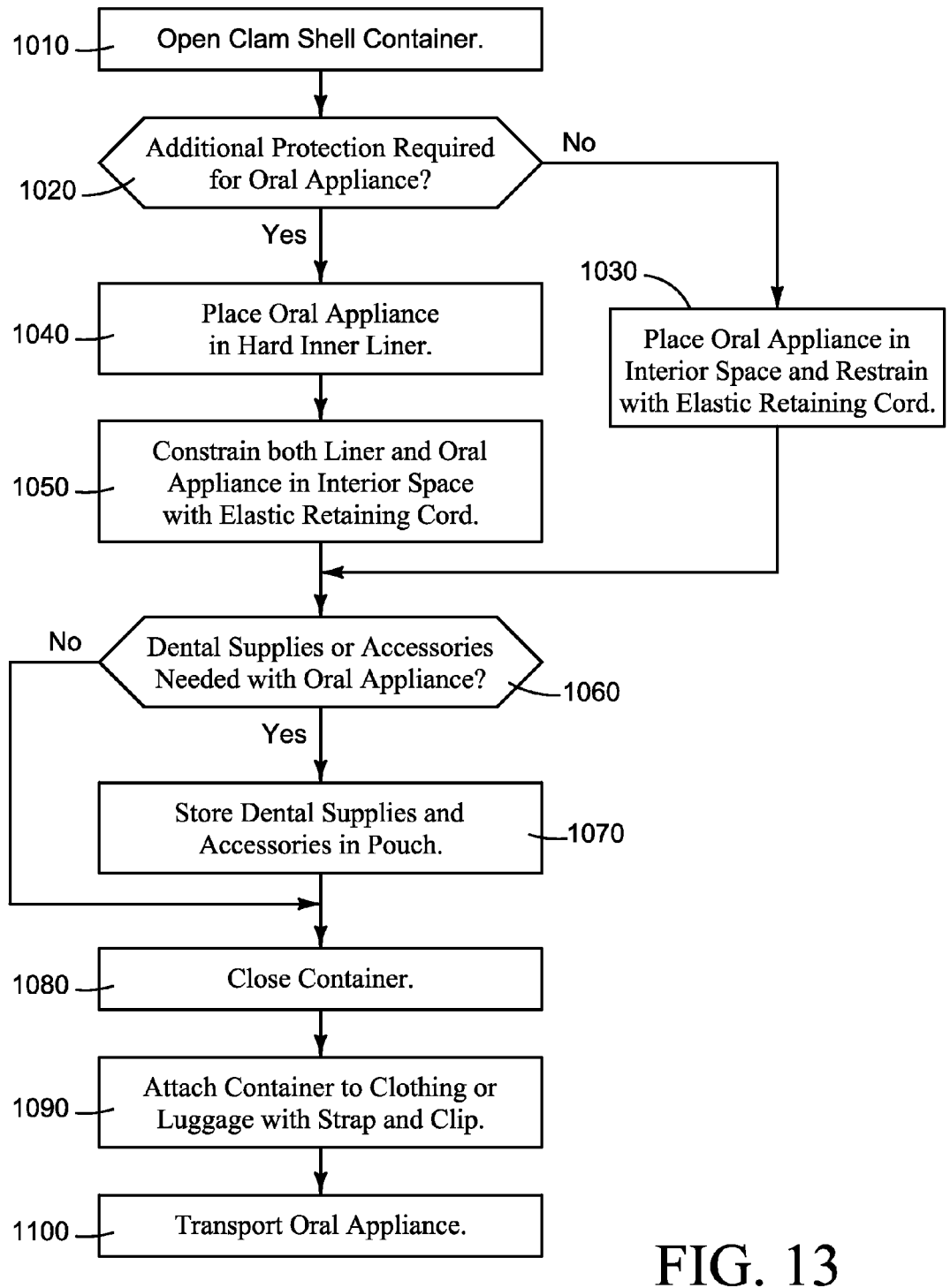
FIG. 13 shows a flow chart demonstrating some of the uses of the protective container.

Some of the uses of the protective container for oral appliances 10 can also be described in flow chart form. In FIG. 13 the user begins by opening the protective container for oral appliances 10 at block 1010. At block 1020 the user decides whether to use a liner for additional protection of the oral appliance 180. If no additional protection is required the user retains the oral appliance 180 in the interior space 112 of the container with an elastic retaining cord 150 at block 1030. If additional protection is required, the user places the oral appliance in a hard inner liner 160 and constrains both the oral appliance 180 and liner 160 in the interior space 112 of the container 10 with the elastic retaining cord 150 at blocks 1040 and 1050. At 1060 the user decides if there are dental supplies or accessories needed for the oral appliance. If dental supplies or accessories are needed, the user stores them in the pouch 170 at block 1070. At block 1080, 1090 and 1100, the user closes the container 10, attaches it to clothing or luggage with the strap 130 and clip 140, and transports the protected oral appliance 180.

It will be appreciated that the invention is not limited to what has been described herein above merely by way of example. Although this invention has been described in terms of certain embodiments, other embodiments that are apparent to those of ordinary skill in the art, including embodiments that do not provide all of the features and advantages set forth herein, are also within the scope of this invention. While there have been described what are at present considered to be the preferred embodiments of this invention, it will be obvious to those skilled in the art that various other embodiments, changes, and modifications may be made therein without departing from the spirit or scope of this invention. Rather, the scope of the present invention is defined only by reference to the appended claims and equivalents thereof.

| Reference | Description/Alternate Terms |
| --- | --- |
| 10 | Container |
| | Clam shell like container |
| | Protective container for oral appliances |

-continued

| Reference | Description/Alternate Terms |
| --- | --- |
| 110 | Outer zip-able cover |
| | Two container halves |
| 112 | Interior of outer zip-able cover |
| | Interior space |
| | Container interior |
| 115 | Zipper, Zipper Handle |
| | Closure |
| 117 | Zipper teeth |
| 120 | Hinge |
| 130 | Strap |
| 140 | Clip |
| 150 | Retaining cord |
| | Elastic retaining cord |
| 152 | Corners of cover halves |
| 160 | Removable hard inner liner |
| | Liner |
| 164 | Removable hard inner liner halves |
| | Clam shell like liner halves |
| 165 | Notch in hard inner container for retaining cord 150 |
| 168 | Liner interior |
| 170 | Mesh net pouch |
| | Pouch |
| 175 | Elastic lip of mesh net pouch |
| 180 | Oral appliance |
| 1010 | Opening clam shell container |
| 1030 | Placing the oral appliance in a closable clam shell like container |
| 1030 | Retaining the oral appliance with an elastic retaining cord |
| 1040 | Placing the oral appliance in a liner |
| 1050 | Constraining the appliance and liner in the interior space w/cord |
| 1070 | Storing accessories in a pouch in the interior space |
| 1090 | Attaching the container to clothing or luggage |
| 1100 | Transporting oral appliance |

Glossary of References Used in Figures

I claim:

1. A protective container for oral appliances comprising:
   two container halves;
   the two container halves joining at a hinge, the hinge spanning between two corners of the two halves to form a clam-shell like container;
   a closure adapted to close the two container halves forming an interior space inside the two container halves;
   an elastic retaining cord in the interior space between the two corners, the elastic retaining cord anchored at both corners;
   a strap having two ends, one end attached to the two container halves; and
   a clip attached to the other end of the strap.

2. The protective container for oral appliances of claim 1 wherein the elastic retaining cord is adapted to retain an oral appliance inside the interior space.

3. The protective container for oral appliances of claim 2 wherein the elastic retaining cord is tensioned across the hinge in the interior space.

4. The protective container for oral appliances of claim 1 wherein the closure is a zipper.

5. The protective container for oral appliances of claim 4 wherein the zipper in a closed position, is located near the strap and clip, facilitating opening of the container when the container is clipped near the waist of the user.

6. The protective container for oral appliances of claim 4 wherein the zipper in a closed position, is located near the strap and clip, such that when the container is clipped near the waist, the oral appliance is accessible without unclipping or repositioning the container.

7. The protective container for oral appliances of claim 1 further comprising a pouch attached in the interior space; the pouch adapted to contain items inside the interior space, the pouch further having an elastic lip.

8. The protective container for oral appliances of claim 2 further comprising a remove-able hard inner liner comprising two clam-shell like liner halves that open and close at a liner hinge; the liner defining a liner interior, the liner adapted to fit into the interior space formed inside the two container halves, the liner further adapted to accommodate the elastic retaining cord inside the liner interior; the elastic retaining cord stretched across the liner hinge within the liner interior to hold the liner within the interior space.

9. A protective container for oral appliances comprising:
   two container halves;
   a hinge joining the two container halves to form a clam-shell like container;
   a closure adapted to close the two container halves forming an interior space inside the two container halves;
   a strap having two ends, one end attached to the two halves;
   a clip attached to the other end of the strap;
   a remove-able hard inner liner comprising two clam-shell like liner halves that open and close at a liner hinge; the liner forming a liner interior, the liner adapted to fit into the interior space formed inside the two container halves;
   an elastic retaining cord inside the interior space; the elastic retaining cord adapted to stretch across the liner hinge within the liner interior to hold the liner within the interior space; and the remove-able hard inner liner further comprising notches at the liner hinge, the notches adapted to allow the elastic retaining cord to enter the liner interior.

10. The protective container for oral appliances of claim 9 wherein the elastic retaining cord is tensioned across the hinge.

11. The protective container for oral appliances claim 9 wherein the closure is a zipper.

12. The protective container for oral appliances of claim 11 wherein the zipper in a closed position, is located near the strap and clip, facilitating opening of the container when the container is clipped near the waistline of a user.

13. The protective container for oral appliances of claim 11 wherein the zipper in a closed position, is located near the strap and clip, such that when the container is clipped near the waistline of a user, the oral appliance is accessible without unclipping or repositioning the container.

14. The protective container for oral appliances claim 9 wherein the remove-able hard inner liner is a single piece of plastic material, the liner hinge being a live hinge.

15. The protective container for oral appliances of claim 9 further comprising a pouch in the interior space; the pouch adapted to contain items inside the interior space, the pouch further having an elastic lip.

16. The protective container for oral appliances of claim 9 further comprising a mesh net pouch in the interior space; the mesh net pouch adapted to contain items inside the interior space, the mesh net pouch further having an elastic lip.

* * * * *